United States Patent [19]
Scholz et al.

[11] Patent Number: 5,342,291
[45] Date of Patent: Aug. 30, 1994

[54] PRINTED WOVEN FIBER MATERIALS AND METHOD

[75] Inventors: Matthew T. Scholz, Woodbury; Michael D. Delmore, Moundsview; Daniel W. Davis, Hugo, all of Minn.

[73] Assignee: Minnesota Mining and Manufacturing Company, St. Paul, Minn.

[21] Appl. No.: 751,725

[22] Filed: Aug. 29, 1991

[51] Int. Cl.$^5$ ............................................. A61L 15/00
[52] U.S. Cl. ...................................... 602/41; 602/44; 602/8
[58] Field of Search ............... 602/41, 42, 43, 44, 602/52, 53, 54, 55, 56, 58; 428/255, 273, 542.8, 913

[56] References Cited

U.S. PATENT DOCUMENTS

| | | | |
|---|---|---|---|
| 2,905,174 | 9/1959 | Smith | 128/156 |
| 3,097,644 | 7/1963 | Parker | 128/157 |
| 3,304,273 | 2/1967 | Stamberger . | |
| 3,351,513 | 11/1967 | Menzer . | |
| 3,383,351 | 5/1968 | Stamberger . | |
| 3,447,887 | 6/1969 | Lindenhovius et al. | 8/55 |
| 3,551,557 | 12/1970 | Garcia | 602/43 X |
| 3,589,934 | 6/1971 | Schimmel | 117/76 |
| 3,970,422 | 7/1976 | Maeda et al. | 8/8 |
| 4,045,601 | 8/1977 | Brodmann et al. | 427/381 |
| 4,125,505 | 11/1978 | Critchfield et al. . | |
| 4,161,176 | 7/1979 | Harris, II et al. | 128/155 |
| 4,175,154 | 11/1979 | Faust et al. | 428/313 |
| 4,175,155 | 11/1979 | Biranowski et al. | 428/313 |
| 4,237,320 | 12/1980 | Krapf et al. . | |
| 4,256,459 | 3/1981 | Russell et al. | 8/471 |
| 4,320,163 | 3/1982 | Schwartz | 428/158 |
| 4,329,176 | 5/1982 | Krapf et al. . | |
| 4,334,530 | 6/1982 | Hassell | 602/42 |
| 4,376,438 | 3/1983 | Straube et al. | 128/90 |
| 4,406,662 | 9/1983 | Beran et al. | 8/471 |
| 4,452,607 | 6/1984 | Wessely | 8/497 |
| 4,455,147 | 6/1984 | Lewis et al. | 8/471 |
| 4,502,479 | 3/1985 | Garwood et al. . | |

(List continued on next page.)

FOREIGN PATENT DOCUMENTS

| | | |
|---|---|---|
| 0556058A1 | 8/1993 | European Pat. Off. . |
| 1140989 | 12/1962 | Fed. Rep. of Germany . |
| 74529 | 7/1970 | German Democratic Rep. . |
| 53-61184 | 6/1978 | Japan . |
| 57-148951 | 9/1982 | Japan . |
| 59-6060 | 1/1984 | Japan . |

(List continued on next page.)

OTHER PUBLICATIONS

Kuehin et al., *Kirk-Othmer Encyclopedia of Chemical Technology*, John Wiley & Sons; New York, NY; Third Edition, vol. 8, 280–350 (1979).
*Kirk-Othmer Encyclopedia of Chemical Technology*, John Wiley & Sons; New York, NY; Third Edition, vol. 13, 374–397 (1981).
*The Pantone Matching System*, Pantone, Inc; New Jersey; 7th printing (1989–1990).
"Ace" Brand Elastic Bandage.
"Delta-Lite 'Flash-Cast' Casting Tape" (A bulletin of Johnson & Johnson Orthopaedics).
"Dyed Glass Fibre Yarns for Textile Wall Coverings"

(List continued on next page.)

Primary Examiner—Danton D. DeMille
Assistant Examiner—Sam Rimell
Attorney, Agent, or Firm—Gary L. Griswold; Walter N. Kirn; Dale E. Hulse

[57] ABSTRACT

A casting tape comprising a fabric substrate with pigment bound thereto is provided. The preferred fabric substrate comprises inorganic material such as fiberglass. The preferred pigments are selected such that they will not interfere with shelf stability of the orthopedic casting tape. The preferred pigments are those selected from the group consisting of Colour Index Pigments Blue 15.3; Red 202; Green 7; Red 166; Red 178; Yellow 109; Violet 23; Red 242; Red 122; Red 124; Black 7; White 6; Violet 19; Violet 42; and, mixtures thereof. Methods for preparing preferred orthopedic casting tapes are also provided.

35 Claims, 3 Drawing Sheets

U.S. PATENT DOCUMENTS

| | | | |
|---|---|---|---|
| 4,563,184 | 1/1986 | Korol | 602/52 |
| 4,609,578 | 9/1986 | Reed . | |
| 4,667,661 | 5/1987 | Scholz et al. . | |
| 4,774,937 | 10/1988 | Scholz et al. . | |
| 4,781,725 | 11/1988 | Dunn, Jr. et al. | 8/471 |
| 4,898,159 | 2/1990 | Buese et al. . | |
| 4,900,614 | 2/1990 | Mayazato et al. | 428/251 |
| 4,934,356 | 6/1990 | Klintworth, Jr. | 128/90 |
| 4,965,126 | 10/1990 | Abraham et al. | 602/52 X |
| 4,968,542 | 11/1990 | Gasper et al. | 428/76 |
| 5,000,172 | 3/1991 | Ward | 602/52 |
| 5,048,513 | 9/1991 | Reinhardt | 602/43 |
| 5,052,380 | 10/1991 | Polta | 128/90 |
| 5,088,484 | 2/1992 | Freeman et al. | 602/44 |
| 5,120,325 | 6/1992 | Dow, Jr. | 602/41 X |

FOREIGN PATENT DOCUMENTS

| | | | |
|---|---|---|---|
| 59-93347 | 5/1984 | Japan . | |
| 63-12768 | 1/1988 | Japan . | |
| 64-14377 | 1/1989 | Japan . | |
| 64-85659 | 11/1989 | Japan . | |
| 2-41475 | 2/1990 | Japan . | |
| 2-102215 | 4/1990 | Japan . | |
| 3-45263 | 2/1991 | Japan . | |
| 3-215268 | 9/1991 | Japan . | |
| 4-11068 | 1/1992 | Japan . | |
| WO90/14060 | 11/1990 | PCT Int'l Appl. | A61F 13/04 |
| 878838 | 11/1987 | South Africa . | |
| 1443796 | 7/1976 | United Kingdom | C08G 18/14 |
| 1550661 | 8/1979 | United Kingdom | B05D 1/36 |
| 1584117 | 2/1981 | United Kingdom | B05D 1/28 |

OTHER PUBLICATIONS (Glaswerk Schuller GmbH), Intern Textile Bull Weaving, Issue 1, pp. 65–66 (1982).

R. B. Hinton, "Glass Fiber–Glass Fiber Fabrics Carving a Broader Niche in Commercial and Industrial Applications", Industrial Fabric Products Review/Buyers Guide (1982).

*Pigment Handbook*, vol. 1, page vii, Properties and Economics, Second Edition, edited by Peter A. Lewis (John Wiley and Sons 1988).

*Transfer Printing Manual*, Chapter 10, pp. 55–65, edited by Charles Reichmann, National Knitted Outwear Association, New York, NY (1976).

PRINTED WOVEN FIBER MATERIALS AND METHOD

FIELD OF THE INVENTION

The present invention relates to printed, fiber materials and methods of preparing them. In particular, the preferred applications of the invention concern fiberglass materials and methods of printing thereon. A particular embodiment described is printed orthopedic casting tapes. The invention also concerns compositions usable for the printing of materials such as knitted fiberglass fabric used in orthopedic casting tapes.

BACKGROUND OF THE INVENTION

While the methods, compositions and materials presented herein may be used in a variety of applications, they were specifically developed with respect to orthopedic casting tapes. Therefore, as background, characterizations of technology relating to orthopedic casting tapes and problems overcome by the present invention are provided.

Orthopedic casting tapes have been produced using curable resins coated on a substrate. Typically, the casting tape is stored as a roll, in a water impermeable storage pouch, until needed for use. It is then removed from the pouch, cut to length, if necessary, and soaked with water. Generally, the tape includes a resin therein which is water-curable, and thus shortly after the tape is dipped in water it begins to cure and harden. The medical personnel, applying the tape to a patient, apply the casting tape immediately after it has been soaked with water. Generally, resin materials are chosen which will begin to set within a few minutes after the soaking with water, and which will harden sufficiently to be weight bearing within about 15 to 30 minutes.

Examples of such orthopedic casting tapes are described in U.S. Pat. Nos. 4,667,661 and 4,774,937 to Scholz et al., the disclosures of which are incorporated herein by reference. U.S. Pat. Nos. "661 and "937 are both owned by Minnesota Mining and Manufacturing Company of St. Paul, Minn., the assignee of the present invention.

Orthopedic casting tapes of the type briefly described above are commercially available. For example, Scotchcast®2 casting tape; Scotchcast® PLUS casting tape and Scotchcast®3 casting tape, are available from 3M Company.

In general, it is desired that the casting tape be constructed from a fabric or substrate which is relatively stretchable; i.e., which has an extensibility of at least about 15 to 25 percent, preferably at least about 20 percent, once coated with the uncured resin. This will facilitate fitting the casting tape around contoured portions of the body, such as the heel, knee or elbow. A preferred fiber material from which such stretchable casting tapes can be formed is fiberglass. Fiberglass woven or knitted substrates usable in casting tapes such as those of U.S. Pat. Nos. "661 and "937 include the knitted substrate of Scotchcast® PLUS casting tape, which tape is available from 3M Company, St. Paul, Minn. Other useable materials include knits having elastomeric yarns, such as Deltalight Conformable (Johnson and Johnson). A resin-coated extensible heat-set fiberglass knit tape, of a type useable in applications of concern herein, is described in U.S. Pat. No. 4,609,578, incorporated herein by reference.

As indicated generally above, typical orthopedic casting tapes comprise a substrate having a curable resin coated thereon. The resin generally includes such additives as lubricants and defoaming agents therein. The lubricants will facilitate unrolling, application and molding of the orthopedic casting tape, without the resin (prior to setting) interfering. The defoaming agents act to increase cast strength and porosity.

A market demand has arisen for the provision of items such as orthopedic casting tapes which are provided with a decorative presentation. Decorations desirable for such constructions include, for example, solid colors, prints and multicolored decorations. A need has therefore arisen for the development of methods and materials for generating such decorations on fabric materials such as those used in preferred orthopedic casting tapes.

SUMMARY OF THE INVENTION

According to the present invention there is provided a casting tape which includes printing thereon. Preferably the casting tape is formed from a material such that it is at least about 15% extensible, and preferably at least about 20% extensible. The preferred casting tape comprises a fabric substrate, a pigment bound to the substrate in a preselected pattern and an uncured, preferably water curable, resin which has been coated on the substrate, typically over the preselected pigment portion. The preferred fabric substrate comprises a knitted substrate of inorganic fibers, preferably fiberglass. The terms "printing", "printed pattern" and variants thereof, as used herein, are meant to include solid color prints; patterns; printed words or symbols; decorations and any similar ink patterns that may be created by printing. The term is meant to exclude patterns created by merely dyeing the substrate; although printed patterns created by printing an ink which comprises color chips including dye therein are included within the scope of these terms and this invention. The term "preselected" and variants thereof, as used in this context, is meant to refer to a printed pattern (even if solid color) which was intentionally (as opposed to randomly) created by a printing process.

The preferred resin coating comprises an isocyanate-functional polyurethane prepolymer. Preferably the resin coating includes therein an effective amount of a stable dispersion of hydrophobic polymeric materials. By "effective amount" in this context is meant an amount sufficient to provide one or more of the benefits of such an additive, as described herein.

According to the present invention a preferred, preselected pattern of pigment involving a multicolored pattern or printing can be provided. Preferred pigments for providing the pattern are those comprising Colour Index Pigments Blue 15.3; Red 202; Green 7; Red 166; Red 178; Yellow 109; Violet 23; Red 254; Red 122; Black 7; White 6; Violet 19; violet 42; and, mixtures thereof. In certain preferred applications the pigment is provided in the chip form, i.e. immobilized in a resin matrix. This latter form is especially favored if the pigment comprises a dye.

Preferably the pigment bound to the substrate is provided substantially free of those metal or metallic ions, which can catalyze cure of the resin system and reactive basic groups such as tertiary amines. Also, preferably the pigments are provided in a form substantially free from potentially reactive active hydroxy groups.

Pigments having metals or metal ions therein are acceptable, however, if the metals or metal ions are not of a type, or are not presented in a form, likely to catalyze premature cure of the resin system. Thus, inorganic pigments such as titanium dioxide and iron oxide ($Fe_3O_4$) may be used in some applications.

In preferred applications, the pigment is bound to the substrate with a binder selected from the group consisting of acrylic and polyurethane resins, polymers made from ethylene vinyl acetate, polyvinyl alcohol, polyvinyl pyrrolidone and mixtures thereof, ethylene propylene copolymers, polyisobutlyene, polyisoprene, butyl rubber, natural rubber, synthetic rubber, polyesters and mixtures of these materials. Such binders can be provided in a form effective to retain the pigment in place on the substrate, without interference with the resin coating.

Preferably, casting tapes according to the present invention are provided in a shelf stable form, i.e. stable for about 1–5 years when provided in a roll form and in a water tight pouch system such as an aluminized plastic pouch. By "stable" in this context it is meant that unacceptable premature cure does not take place and the printed pattern is provided such that it does not unacceptably blur, bleed or otherwise disperse during the storage period.

Also according to the present invention, a method is provided for preparing an orthopedic casting tape, the method generally comprising steps of providing a knitted inorganic fiber substrate; printing a pigment pattern on the substrate to form a printed substrate; and, applying an uncured resin coating to the printed substrate, typically over the print if applied on the same side of the substrate as the print. Preferred methods involve utilization of the material described above for the preferred casting tape. A variety of printing methods may be used, as explained herein below. The preferred printing process, presently foreseen, is flexographic printing. Such processes may be used to readily provide preferred multicolor printed patterns.

Also according to the present invention, there are provided orthopedic casting tapes and cured articles prepared according to the preferred application or methods. Such tapes may be readily provided in attractive, shelf stable, forms.

DETAILED DESCRIPTION OF THE INVENTION

Figure 1:
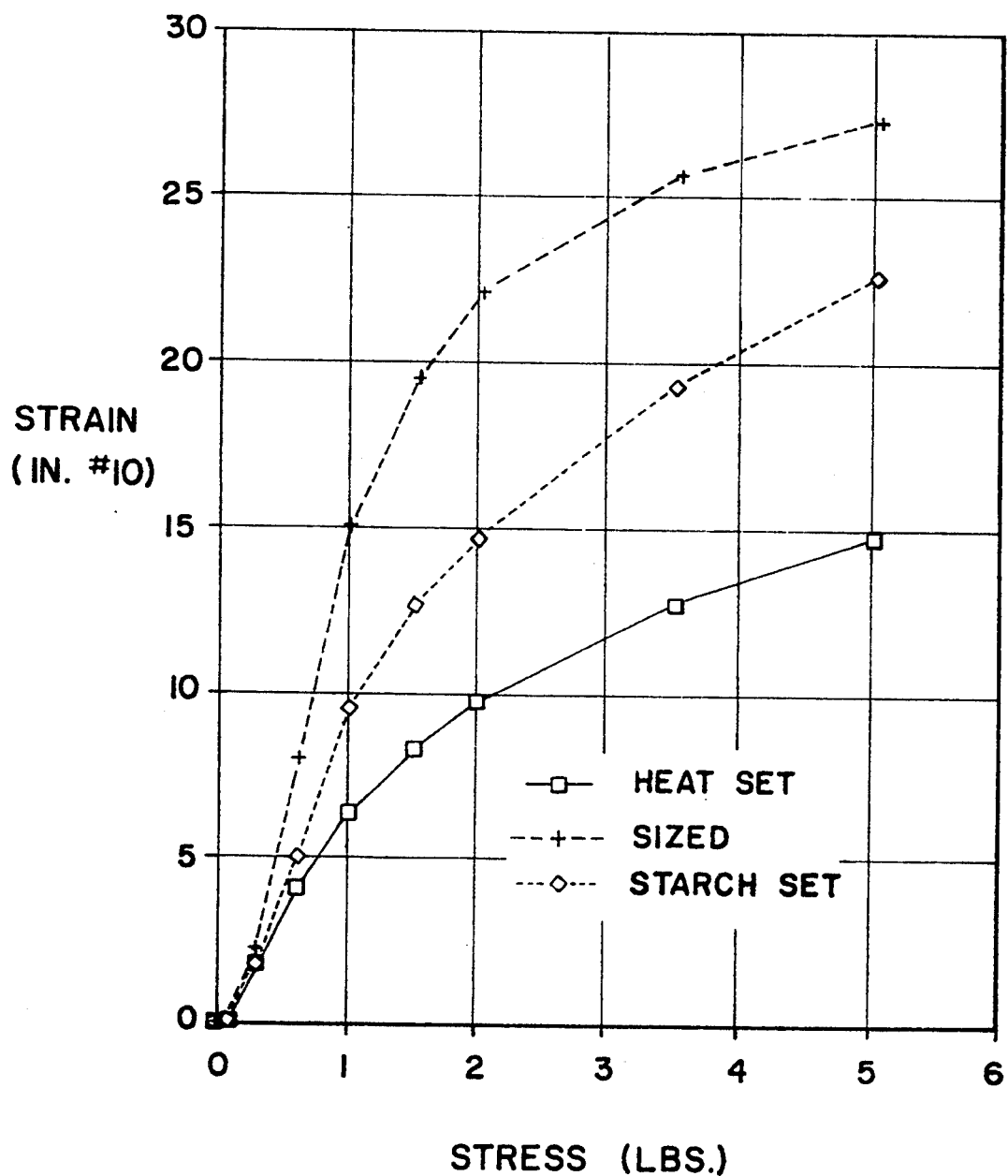
FIG. 1 is a graph representing stretchability of certain substrates useable in applications of the present invention.

According to the present invention there are provided methods for printing items onto a woven or nonwoven fabric, preferably the substrate of a knitted or woven fabric orthopedic casting tape; and, materials for use as an ink to accomplish such printing. The invention also concerns the provision of an orthopedic casting tape, and a cured article, with printing thereon. The methods, materials and compositions may be used, for example, to generate multicolor prints, including prints which are prepared with registration.

As indicated by the general descriptions herein, the methods and compositions of the present invention may be utilized in association with orthopedic casting tapes of a wide variety of types, including ones involving a variety of fabric materials. However, the invention was particularly developed around, and to accommodate, problems associated with providing printing on orthopedic casting tapes having substrates formed from fiberglass. Thus, herein certain particular problems associated with the concept of providing a printed fiberglass substrate and orthopedic casting tape will be briefly examined.

Fiberglass Orthopedic Casting Tapes Generally

Knitted fiberglass materials are particularly desirable substrates for use in orthopedic casting tapes. Fiberglass is relatively strong, inexpensive, and, when used with an appropriate curable resin, will set to a very hard, lightweight, strong, weight-bearing cast. While fiberglass yarns are relatively inelastic, they can be knitted into a highly extensible knit fabric or substrate having an extensibility of at least 15–20 percent, or more. A knitted fiberglass substrate useable in orthopedic casting tapes is described in Reed U.S. Pat. No. 4,609,578 incorporated herein by reference.

Consider the problem of providing an orthopedic casting tape having such a substrate, with a printed or colored image, field, pattern or decoration thereon. The substrate will need to be coated with a selectively curable resin, before being rolled and packaged. Typically a water curable resin is used. If currently preferred liquid curable casting resins are used, when the colored image is provided on the construction after the resin has been applied, the image will be dispersed in the resin coating and will not be immobilized on the substrate. Thus, one would expect the colored image to disperse (i.e., blur) in the resin, with time. Furthermore, since typical products are sold in roll form without the use of liner, transfer of the dye could occur between layers. It is practical, then, to conclude that the colored image or pattern should be applied to, and be bonded to, the substrate before the resin is applied thereto.

Fiberglass is an inorganic material. Thus, typical organic dyes will not penetrate into it. The colored pattern, then, cannot be applied as a dye expected to penetrate into the yarns of the fabric in a defined pattern and to retain that pattern.

In addition, the pigment applied to the substrate should be such as to be relatively insoluble in the resin coating (uncured) later to be applied. If the pigment is substantially soluble in the uncured resin, after the printed substrate is coated with the resin the pigment of the printed pattern will tend to dissolve and disperse in the resin, blurring the image unacceptably. With respect to this, one is reminded that the resin coating will remain in place, uncured, for the shelf life of the product, which may be 1–5 years. Thus, there will be plenty of time for blurring (bleed) to occur, before use. Also, the product will typically be stored in a rolled form, which can exacerbate blur or bleed by transferring one layer to an adjacent layer.

In addition, typically a binder will be used to bind the pigment(s) to the substrate. The binders should also be relatively insoluble in the uncured resin, to inhibit pigment dispersion, bleed or blur.

It is again noted that the pigment applied to the fiberglass fabric will not penetrate the fibers or filaments of the fabric, but rather, along with the binder, will generally occupy a position on the fabric outer surface. As a result, it is relatively available for reaction with the later applied resin. If the pigment is unacceptably reactive, or includes reactive moieties or contaminants therein, or catalyzes side reactions or contains contaminants which catalyze side reactions, it will lead to premature and/or unacceptable cure of the resin, i.e., inappropriate (shortened) shelf life. In addition, reaction with the resin may cause color change or fade, in the printed pattern.

A particular problem is presented by the concept of printing a "stretchable" fabric, i.e., a fabric having an extensibility of at least about 15 percent in the machine direction when measured using 1.5 lb. per inch width (1.75 kg/cm) of fabric. Multicolored patterns (or any pattern requiring multiple printing stations) are difficult to print, since the material may tend to stretch as it moves through the printing apparatus, preventing or inhibiting alignment between multicolored portions. Similarly, registered patterns i.e. patterns which require relatively precise alignment between multiple print stations (multicolored or not) may be difficult to predictably and reproducibly create. However, certain techniques of the present invention can be applied to obtain printed casting tapes having extensibility of 15–20% or more.

Printing Inks

According to the present invention, printing inks are provided which can be applied to stretchable substrates such as fiberglass substrates in a selected pattern and which will remain thereon even after an overcoating of a curable liquid resin (such as a resin utilizable in an orthopedic casting tape) is applied. The preferred printing inks will generally not appreciably react with the resin and/or unacceptably affect storage stability. In general, an orthopedic casting tape as described herein is considered storage-stable if it does not appreciably cure (i.e. cure to the point it is not useable) within six months to a year, after being sealed in a watertight aluminum foil laminate (common to the industry) and stored under ambient conditions. Preferably it is storage-stable for at least 3 years and most preferably for at least 5 years.

Preferred printing ink compositions according to the present invention comprise one or more pigments dispersed in a vehicle which serves as a carrier. The term "pigments" as used herein is intended to include within its scope (but is not limited to) colorants which are essentially insoluble in the curable resin as well as dyes or other colorants which have been molded into an insoluble color chip form. The term "chip" as used herein in this context is meant to refer to a dispersion of colorant in a solid resin matrix which has been converted to a powder for use as a pigment.

The printing inks useful in the present invention typically include one or more pigments, a vehicle (carrier) and a binder, for binding the pigment to the inorganic substrate (preferably fiberglass). Preferred printing inks include one or more of the following adjuvants in effective amounts: thickeners; defoamers; pH regulators; and, plasticizers.

Preferred printing inks according to the present invention are provided substantially free of trace metal ions of a type that can cause premature hardening or cure of the resin overcoat. Especially certain forms of mercury, tin, zinc, iron, sodium and potassium ions are to be avoided. However, certain inorganic pigments such as titanium dioxide and iron oxide ($Fe_3O_4$) are acceptable, since the metal ions are in a form not likely to catalyze premature cure. In addition, preferably printing inks according to the present invention include therein pigments substantially free of carboxylic acid salts or moieties. By "substantially free" in either context, a functional definition in intended; i.e., the material is sufficiently free so that premature cure (loss of acceptable shelf life or storage stability) is avoided.

In addition, preferred printing inks according to the present invention are provided substantially free of residual base, including inorganic bases, such as sodium hydroxide and potassium hydroxide; and, basic groups within the pigments, such as tertiary amines, which could catalyze premature setting or cure of the resin applied to the construction after the printing ink is positioned on the substrate. By "substantially free" in this context, again an operational definition is intended. That is, preferably the printing ink is sufficiently devoid of such material that premature cure or unacceptable loss of storage stability (shelf life) of the orthopedic casting tape is avoided. Preferably the organic compound(s) which make up the pigment(s) is completely free of such moieties.

Further, preferably pigments substantially free of active hydrogen compounds are avoided, since they might tend to react into the resin coating. By "substantially free" in this context, a functional definition similar to that given above is intended. By "reactive hydrogen" in this context, it is meant that the group, including hydroxyl, amine and the like, as defined by the Zerewitinoff test, is available for reaction and not, for example, inhibited therefrom by deactivation or stearic factors.

As explained above, in part preferred printing inks for use according to the methods and constructions of the present invention are definable from an understanding of the preferred resin materials for use with constructions according to the present invention. That is, the printing ink should include therein pigment(s) which is: not very soluble in the resin; not likely to react with the resin; and, which is substantially free of materials or moieties likely to cause premature cure of the resin. For at least these reasons, before preferred printing inks according to the present invention are further defined, a discussion of preferred resin systems and substrates is presented.

Substrates

Preferred substrates useable with the present invention include knitted, woven and non-woven sheet materials which, when coated with the curable resin, exhibit sufficient stretchability for use of an orthopedic casting tape.

The preferred substrate or scrim utilizable in constructions according to the present invention is a substrate having a stretchability or extensibility (at least once it has been flexibilized, i.e. coated with resin) of at least about 15 percent, preferably at least about 20 percent, and most preferably at least about 25%, when measured under a load of 1.5 lb/in (1.75 kg/cm) width. Preferred such materials are knits of inorganic fibrous materials, such as fiberglass. For orthopedic casting applications, it is also important to ensure that the substrate is relatively porous. One such preferred material is the substrate used in Scotchcast®3 casting tape, available from 3M Company, St. Paul, Minn. General descriptions of acceptable fabric materials are provided in U.S. Pat. No. 4,609,578.

Resin System

When the application of the present invention is to the provision of an orthopedic casting tape or the like, the preferred resin system (coating) applied to the substrate is a resin system such as described in Scholz et al., 4,667,661; Scholz et al., 4,774,937; and South African Pat. No. 90/4053, the disclosures of which are incorporated herein by reference. The preferred resins are those cured by water. The preferred water-curable resins are isocyanate-functional polyurethane prepolymers formed by the reaction of a polyisocyanate with a polyfunctional active hydrogen compound such as a polyether or polyester polyol. The most preferred water curable polyurethane prepolymer resins, as disclosed in the Scholz et al. patent, are formed by the reaction of a polyol with an excess of polyisocyanate. The preferred isocyanates are those derived from diphenylmethane 4,4'-diisocyanate. The most preferred isocyanate is Isonate 2143L (Dow Chemical). The resins disclosed in the two Scholz et al. U.S. patents also include tack reducing agents, which facilitate application of the orthopedic casting materials. However, it is preferred in the present invention that the resins be modified by using a polyol (which represents at least a part of the total polyol concentration employed) having a stable dispersion of hydrophobic polymeric particles therein, as described in South African Pat. No. 90/4053 incorporated herein by reference. The particles serve to: (1) reduce foaming during cure; (2) decrease the set times; and/or (3) result in cured materials having greater strength and layer to layer lamination, in particular greater warm wet strength. Preferred embodiments provide one or more of the foregoing benefits, while the most preferred embodiments provide all three of the foregoing benefits.

Again, the preferred resins are those cured with water. A number of classes of water-curable resins are known, including polyurethanes, cyanoacrylate esters, and, when combined with moisture sensitive catalysts, epoxy resins and prepolymers terminated at their ends with trialkoxy or trihalo-silane groups. For example, U.S. Pat. No. 3,932,526 discloses that 1,1bis(perfluoromethylsulfonyl)-2-aryl ethylenes cause epoxy resins containing traces of moisture to become polymerized.

Resin systems other than those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol), may be used. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Preferably, the hydrophobic polymeric particles are made from vinyl monomers. However, in general any monomer or combination of monomers may be employed which will form hydrophobic polymeric particles that remain in a stable dispersion with the resin. Examples of polymeric particles which have been found suitable for purposes of the present invention are those made of polyacrylonitrile, a copolymer of acrylonitrile and styrene, and an N-substituted polyurea (formed, for example, from toluene diisocyanate and ethylenediamine). Polymer particles containing polyols made from epoxy-based resins or combinations of any of the foregoing may also be used to form the polymeric particles used in the present invention.

Several polyols are commercially available which already have such polymeric particles dispersed therein, and are thus suitable for practice of the present invention. For example, Niax E-562 polyol (available from West Virginia Polyols Corp., Wheeling, West Virginia) which contains polymeric particles made of a copolymer of acrylonitrile and styrene (in a 50/50 weight-percent ratio); Niax E-701 polyol (also available from West Virginia Polyols Corp.) which contains polymeric particles made of polyacrylonitrile; and, Multranol 9151 polyol (available from Mobay Chemical Corp., Pittsburgh, Pa.) which contains polymeric particles made of polyurea, have all been found to be useful in practicing the present invention.

At present, the most preferred polyols having polymeric particles dispersed therein are the aforementioned Niax E-562 and Niax E-701 polyols, which are referred to by West Virginia Polyols Corp. as "Niax Performance Polyether Polymer Polyols".

The preparation of polymeric particle containing polyols is described in U.S. Pat. Nos. 3,304,273; 4,125,505 and 3,383,351; all of which are incorporated herein by reference. These methods of preparation may be utilized to form the desirable polymeric particle containing polyols used in resin compositions according to the present invention.

The curable resins of the present invention may be used with a variety of well-known scrims for use as orthopedic casting materials or for other applications. Although many materials are well-known for this purpose, fiberglass is presently preferred. In this regard, in one presently preferred embodiment of the present invention, the scrim comprises an extensible, heat-set knitted fiberglass fabric as set forth in U.S. Pat. No. 4,609,578 (Reed). One example of a knitted fiberglass scrim which is within the scope of U.S. Pat. No. 4,609,578 is available from 3M, St. Paul, Minn. as the scrim component of Scotchcast® 2 casting tape. The Scotchcast® 2 scrim could be obtained by solvent washing to remove the resin from this commercially available casting tape.

Orthopedic casting materials, involving water-curable resins, prepared in accordance with the present invention are applied to humans or other animals in the same fashion as other known orthopedic casting materials. First, the body member or part to be immobilized is preferably covered with a conventional cast padding and/or stockinet, for protection. Next, the curable resin is activated by dipping the orthopedic casting material in water. Excess water is then squeezed out of the orthopedic casting material, and the material is wrapped or otherwise positioned around the body part so as to properly conform thereto. Preferably, the material is then molded and smoothed to form the best fit possible and to properly secure the body part in the desired position. Although often not necessary, if desired the orthopedic casting material may be held in place during cure by wrapping an elastic bandage or other securing means around the curing orthopedic casting material. When curing is complete, the body part is properly immobilized within the formed orthopedic cast or splint.

Preferred Printing Inks

The preferred printing inks for use in the present invention comprise at least a pigment and a binder. The purpose of the pigment is to impart color to the design. The pigment will be exposed to the uncured liquid resin, in the rolled-up product, for an extended period of time, for example sometimes up to five years or longer. Therefore, the pigment should be both insoluble in the uncured resin and incapable of causing undesirable side reactions of (or with) the resins, which could tend to limit shelf life, fade, bleed or otherwise cause deterioration of the printed pattern.

For the preferred isocyanate-functional polyurethane prepolymer resins used in orthopedic casting tapes, and described above, the pigments are preferably relatively high in molecular weight (to reduce solubility in the resin) and preferably are substantially free of heavy metals or metal ions (which could catalyze premature cure of the resin) or highly basic tertiary amines (i.e., those with a pKa greater than about 9 and which again might tend to catalyze cure of the resin and reduce shelf life). It has been observed that pigments having conjugated aromatic rings therein are often preferred, since they tend to be relatively insoluble in the resin.

Some commercially available pigments contain active hydrogen functionalities, which are potentially reactive with isocyanate groups. Since in application the pigments of the present invention are insoluble and often dispersed in the resin matrix (called a "color chip"), it is not convenient or necessary to determine whether the pigment is reacting slightly with the resin. As long as no significant color change, aging or limitation of shelf life occurs the pigment reactivity is generally not a problem.

Preferred pigments for use in printing inks according to the present invention comprise those within the following chemical classes: phthalocyanine; dioxazine; diazo; anthraquinone (vat dyes); quinacridone; perylene; and, isoindolinone. Presently, the preferred pigments are "high performance" or "automotive grade" pigments. The specific preferred pigments include Colour Index Pigments such as Blue 15.3; Red 202; Green 7; Red 166; Red 178; Yellow 109; Violet 23; Red 242; Red 122; Red 254; Black 7; White 6; Violet 19; Violet 42; and, mixtures thereof. The Colour Index is published by the Society of Dyers and Colourists and the American Association of Textile Chemists and Colorists, Third Addition; incorporated herein by reference. These pigments, and mixtures of them, may be utilized to provide a variety of selected colors or hues in printing patterns applied to constructions according to the present invention. Certain of the pigments may be alternately defined by their Colour Index Constitution number (in parentheses) as follows: Blue 15.3 (74160); Green 7 (74260); Red 178 (71155); Violet 23 (51319); Red 122 (73915); Black 7 (77266); White 6 (77891); and, Violet 19 (73900).

Certain of the above-listed Colour Index pigments may be alternatively identified as follows:

| Color Index Pigment Number | Chemical Description |
|---|---|
| Blue 15.3 | Copper Phthalocyanine Blue of the beta crystal form |
| Green 7 | Polychloro Copper Phthalocyanine Green |
| Violet 23 | Dioxazine Violet: 3-Amino-9-ethylcarbazole condensed with chloranile |
| Red 122 | Perylene Vermillion: 3,4,9,10 perylene-tetracarboxylic anhydride condensed with p-ethoxyaniline |
| Red 166 | Diazo Scarlet: Diazotized 2,5-dichloroaniline coupled with 3-hydroxy-2-napthalene-carbonyl chloride + 2 moles diamino benzene |
| Red 178 | Perylene Red: 3,4,9,10 perylenetetra-carboxylic anhydride condensed with p-phenylazoaniline |
| Yellow 109 | Tetrachloroisoindolinone Yellow G: derivative of 4,5,6,7-Tetrachloro-isoindoline-1-one |

One manner in which pigments according to the present invention need be applied, is through development of a Pantone Color scheme. The Pantone Color Formula Guide is a guide which assists ink manufacturers and formulators to achieve a specific shade of a specific color. The Pantone Color Formula Guide begins with nine basic colors: Pantone Yellow; Pantone Warm Red; Pantone Rubine Red; Pantone Rhodamine Red; Pantone Purple; Pantone Reflex Blue; Pantone Process Blue; and, Pantone Green. For an ink manufacturer to be able to match the hundreds of colors in the guide, it is first necessary to formulate an ink which matches each basic color. For each basic color there are a number of potential pigments which may be able to yield the correct match. Therefore, for ink formulations according to the present invention, it is desirable to identify pigments which can match the basic colors of the Pantone Color scheme.

Once the basic colors are matched, the Pantone Color Formula Guide can be used by the ink manufacturer for two general purposes:

1. Color identification: each color in the guide has a specific pantone color identification number. For example, Pantone 340C is a shade of Green. (The C stands for what the color looks like on coated paper. Some colors end in a U which stands for uncoated paper.) This facilitates communication between the user and ink supplier. The customer can choose a specific color, for example, Pantone 340.

2. Color formulation: the Pantone Color Formula Guide also assists manufacture in achieving a specific color. For example, directly Pantone 340C corresponds to the following: 12 parts Pantone Process Blue 75.0; 4 parts Pantone Yellow 25.0. This means that in order to yield Pantone 340, 12 parts of the ink which matches the basic color Pantone Process Blue should be mixed with 4 parts of the ink which matches the basic color Pantone Yellow (in other words as a 75%/25% mixture). It is noted that this is only a guide and the exact formulation may sometimes differ. In general, Pantone colors are matched by trial and error when using color index pigments.

In certain preferred applications, the pigment is provided in a "chip" form, i.e., it is compounded into a resin matrix. The resin matrix helps to provide light fastness of the pigment, and can also contribute to its chemical resistance once it is in contact with a curable resin. The resin matrices are generally thermoset or preferably thermoplastic materials such as toluenesulfonamide-melamine-formaldehydes; polyesters; acrylics; polyamides; polyurethanes and the like. The compounding may be accomplished in several ways including: milling; incorporating the pigment or dye into an unreacted thermoset composition followed by polymerization and grinding; and adding the dye or pigment to a solvent solution or hot melt of thermoplastic followed by drying and grinding. As indicated above, if a "chip" form is used, the pigment may comprise a "dye", i.e., a color which might be soluble in the curable resin but which can be rendered insoluble by presentation in a chip form. For example, daylight fluorescent colorants can be provided in chip form. (See Kirk-Othmer, *Encyclopedia of Chemical Technology*, 3rd Ed., Vol. 14, pp. 559–561, incorporated herein by reference.)

The ink vehicle is a solvent or carrier for the ink composition. The binder can be any material which is capable of binding the pigment particles to the substrate. The binder should be such that once the ink is dry it is substantially insoluble in the resin, so as to ensure that the printed design does not migrate. It should also be such as to retain the pigment such that it does not migrate independently of the binder.

Further, the ink binder should be such as to not appreciably interfere with the shelf stability of the resin. Thus, it should be "substantially free" of basic groups and certain metals, as previously described for the pigment.

Preferred ink binders are those which maintain adhesion of the pigment to the substrate without significantly decreasing the conformability of the substrate. That is, even with the ink binder thereon the substrate can readily conform to the contours of a patient's body, in use.

Preferred ink binders include those made from acrylic and polyurethane resins; polymers made from ethylenically unsaturated monomers, for example, EVA (ethylene vinyl acetate), PVA (polyvinyl alcohol), PVP (polyvinyl pyrrolidone), ethylene propylene copolymers, polyisobutylene; and, polyisoprene; butyl rubber; natural and synthetic rubber; polyester resins; proteinaceous materials (for example, gelatin, casein); gums and the like.

In some applications of the present invention, the ink may be provided as a hot melt. Thus, the ink binder may be provided in a hot melt form (for example, as polyurethanes, EVA, etc.). The ink binders may also be provided as part of gelation inks (for example, fine particles of PVC resin heated in a plasticizer), radiation curable inks (ultraviolet, infrared or electron beam curable); and, hot transfer inks. The ink binders may also contain plasticizers and other auxiliary chemicals.

Ink binders of the type described above are also disclosed in German Pat. 1,140,898. Relatively small amounts of ink binder are used to remain because the amount of ink needed to print it is a relatively small fraction of the total weight of the articles, i.e., less than one percent. A typical coating weight would be about 0.01–2.0 gram per square meter, generally about 1.5 g/m$^2$ of ink binder.

It is foreseen that both contact and non-contact printing processes may be useful in providing printing constructions according to the present invention. At least the following methods may be used, for example, to create printing constructions according to the present invention: flexographic printing processes; rotogravure printing processes; silk screen; hot melt screen printing; ink jet printing; continuous ink jet; and, electrostatic methods. It will be understood that the particular compositions in the ink may be varied, especially with respect to the binders, vehicles and thickeners, depending upon the printing process chosen. At the present time, flexographic printing processes are foreseen as preferred.

The rheology of the printing inks is very important and to a great extent dependent upon the method of printing chosen. The inks generally will contain thickeners such as alginates, locust bean gum ether, starch ether, cellulose derivatives (for example, carboxymethyl cellulose or carboxyethyl cellulose), polyacrylic acid and copolymers of acrylic acid with other vinyl monomers. Again, the preferred flow characteristics of the inks are obtained and varied depending upon the printing method and apparatus used.

The printing inks may also contain effective amounts of auxiliary chemicals such as defoamers, pH regulators and plasticizers.

The ink carrier vehicle may be either an organic solvent based or aqueous based system. At the present time, aqueous based inks are generally preferred because of their ease of use and stability. They also are preferred because of their low toxicity and low environmental impact. It is also important that the ink be non-irritating and non-sensitizing to human skin.

It is foreseen that in typical applications of the present invention, manufacturers of orthopedic casting tape will not themselves formulate the inks. Rather, the inks will be obtained from commercial ink formulators. The descriptions given above can be utilized to obtain acceptable inks from commercial ink suppliers or formulators.

One commercial ink supplier which can provide inks usable in the present invention is Louis O. Werneke Company of Plymouth, Minn. Their inks provided under the following product codes have been found acceptable for preparation of printed orthopedic casting tapes according to the present invention: SSUY-10001 (yellow); SSR-10002 (red); SSR-10004 (red); SSP-10005 (purple); SSB-10006 (blue); SSB-10007 (blue); SSG-10008 (green); SSY-10013 (violet). From these pigments, a variety of colors and hues can be generated by the ink supplier.

In addition, the commercial ink supplier can typically generate an ink of appropriate rheology for application according to a defined printing process. Thus, for example, the above-defined pigments can be presented by an ink supplier in an ink of appropriate viscosity, etc. for application according to any one of flexographic, rotogravure, silk screen, hot melt screen, ink jet printing, continuous ink jet printing, or electrostatic printing methods. The issue with respect to this primarily concerns solvent, or carrier, viscosity and adjuvants. The above defined and presented list of acceptable binder materials may include components most preferred for a specific chosen method of printing, and the ink formulator will be able to discern this. Hereinbelow, specific examples presenting ink compositions acceptable for use with a variety of printing processes are provided.

Preparation of the Substrate for Printing

As explained above, desirable substrates for use in constructions according to the present invention are somewhat extensible e.g. capable of elongating in both machine and transverse directions. While such materials are desirable as orthopedic casting tapes, they may be difficult to print on. For certain of the printing techniques described herein, it is preferred to prepare the substrate for printing, to facilitate the printing process.

For example, when substrates according to the present invention comprise commercially available knitted fiberglass yarns, they are typically provided with a size or lubricant thereon. Prior to printing, it will generally be desirable to desize and heat set the fabric somewhat, rendering it more stiff prior to printing. This can be done by heat treatment. For example, fiberglass knits comprised of ECDE 75 0/1 0.7 or ECG 75 0/1 0.72 fiberglass yarn (available from PPG Industries) are preferably heat treated at about 750° F. -900° F. (399–482° C.) for at least about 6 to 8 hours, prior to being printed with compositions according to the present invention. This process anneals the yarns and removes the sizing, which stiffens the tape in its uncoated state.

Such a step of desizing and/or heat treatment prior to printing does not render the final composition unacceptably stiff or inflexible since, once the resin is applied over the printed substrate, the substrate becomes reflexibilized. That is, the fluid resin re-lubricates the yarns in the substrate and facilitates their movement relative to one another. The resin may be provided with lubricants therein, to facilitate the process.

In the alternative to heat treatment, if the sizing is a starch or starch/oil sizing, it may be set. For example, such a sizing can be set if first wet with water to dissolve and/or swell the starch and then hardened in a drying process.

In the alternative, a binder may be added to the fabric prior to printing. Such a method is less desirable, since when the hardened sizing is removed from the fabric some of the printing may be removed as well.

The advantages of stabilizing the fabric prior to printing are illustrated in FIG. 1. The figure reflects the amount of strain or stretch (percent) obtainable under a particular stress (stretch load) applied to a preferred 4' wide substrate comprising ECDE 75 0/1 0.7z yarn knit according to the example of U.S. Pat. No. 4,609,578. Curve 1 reflects a substrate which has been heat set at 800° F. for 8 hours. Curve 2 comprises a 4' wide fabric of the same knit construction which has been starch set by saturating with 15 psig saturated steam followed by drying for 12 hours (150° F. or 65.6° C.). Curve 3 reflects a non-stabilized 4" wide substrate of the same knit construction. It is apparent that, for example, stabilizing the substrate by heat set leads to considerably less stretchability, under an applied stress. Via such stabilizing techniques, then, relatively extensible fabric such as a knitted fiberglass fabric can be rendered sufficiently stabilized to process well in printing processes such as flexographic printing processes. Again, after the printing process the substrate can be rendered again sufficiently flexible for desirable uses in orthopedic casting tape, by coating it with the curable resin, which relubricates the yarns.

It would also be possible to incorporate a nonextensible carrier web such as a liner. This method is generally not preferred, due at least to cost.

EXPERIMENTAL EXAMPLES

Example 1. Screen Printing

A mixture of 2% by weight Heliogen Blue K 6911D phthalocyanine pigment (available from BASF Wyandotte Corp., Holland, Mich.) and 98% Pellethane 2103-70A polyurethane (available from Dow Chemical, Midland, Mich.) was compounded and dried overnight at 130° C in a convection oven. One part of this dried mixture was combined with about four parts (three to five) of HC 2112 PMOO -41 hot melt adhesive (available from H.B. Fuller Co., Minneapolis, Minn.) and applied from a Graco Microprint Screen Printer with a Graco Dynamelt 400 hot melt pump (available Graco/LTI, Monterey, Calif.) onto a strip of 4 inch wide (10.2 cm) heat set (425° C. for 8 hrs.) desized fiberglass knit fabric (described in the example of U.S. Pat. No. 4,609,578). This printing was carried out at a melt temperature of 375° F. (191° C.), a screen temperature of 385° F. (196° C.) and a bar temperature of 375° F. using a custom made 40 mesh screen. The patterns provided by the screen consisted of lettering (printing which read DON'T HAVE A COW MAN), figures (elephants and dinosaurs) and geometric shapes (circles, triangles and squares) and were all clear and well-defined. The printed tape was hand coated with a casting resin described in Table 1 below to a resin weight of 42.5% by weight in a low humidity (less than 6% relative humidity) environment and rolled up onto a 0.75 inch (1.9 cm) polyethylene core for storage in an aluminum foil laminate pouch.

After coating with the casting resin and storage in the pouch for several days, the sample was removed and applied to a 2 inch (5.1 cm) diameter mandrel. The printed pattern was well defined, with no evidence of bleeding or reduced shelf stability.

TABLE 1

| CHEMICAL | EQ. WT. | WT. % | GRAMS |
|---|---|---|---|
| ISONATE 2143L | 144.0 | 56.4 | 1974 |
| BENZOYL CHLORIDE | 141.00 | 0.05 | 1.75 |
| DB-100 | | 0.18 | 6.3 |
| IONOL ® | 248.00 | 0.48 | 16.8 |
| MEMPE | 129.50 | 1.32 | 46.2 |
| PLURONIC F-108 | 7250.00 | 4.00 | 140.0 |
| NIAX POLYOL PPG-425* | 215.95 | 12.7 | 445.2 |
| NIAX POLYOL PPG-725* | 384.56 | 24.8 | 869.1 |
| TOTAL | | | |
| NCO/OH RATIO: | 3.15 | | |
| NCO EQUIV. WT.: | 375.00 | | |
| OH EQUIV. AVG.: | 335.02 | | |

*Available from A.C. West Virginia Polyols Corp.

Example 2. Flexographic Printing with Water-Based Inks

A 225 yard (206 meter) roll of four inch wide (10.2 cm) heat set desized fiberglass knit fabric of Example 1 was printed with Solvent Safe Blue 7 aqueous based ink (available from Louis O. Werneke Company, Plymouth, Minn.). The printer was a Mark Andy Model 820 printing press (available from Mark Andy Co., St. Louis, Mo. using a CYNEL flexographic plate C.E.I. DuPont DeNemours, Wilmington, Del.) in combination with 400 ceramic anilox roll (available from STORK CELLRAMIC INC., Milwaukee, Wis.) and 65 durometer metering roll. A flexographic plate was used to print (a graphic lettering image) and the nip pressure used was somewhat (about 20 to 100%) greater than that ordinarily used to print paper products to provide an appealing image. The press speed was about 50 to 100 feet per min. The entire roll was then coated, using a curtain coating technique in a dry atmosphere (less than 6% relative humidity) with the resin described in Example 1 to a resin weight of 42.5%, in a dry environment. The tape was converted into 4 yard (3.66 m) rolls which were sealed in aluminum foil laminated pouches. After about 2 hours a roll was removed from its pouch, dipped under water, squeezed 3 times, removed from the water and squeezed to remove excess water wrapped around a 2 inch (5.1 cm) diameter mandrel and allowed to cure. The cured product clearly showed the printed design. Additional printed rolls were placed in a 150° F. (65.5° C.) oven in an accelerated aging test for 4 weeks. No macroscopic changes such as bleeding of the ink or premature curing were observed.

Example 3. Flexoqraphic Printing with UV Curable Ink

A 255 yard (206 meter) roll of the four inch wide (10.2 cm) heat set, desized fiberglass fabric used in Examples 1 and 2 was printed with LT 1208 black ultraviolet curable ink (available from Louis. 0. Werneke Company, Plymouth, Minn.) on the printing apparatus described in Example 2 except that the Cynel plate used was a test plate consisting of lettering of different sizes as well as a figure. The ink was cured after printing by exposure, in a 10 inch (25.4 cm) section while moving on the belt at a speed of about 50 to 100 feet per min., to a Fusion ultraviolet lamp of 300 watt/square inch (available from Fusion Systems Inc., Rockville, Md.). The plate provided printing of a variety of lettering sizes and shapes, and an increase in the nip pressure and the belt speed resulted in bolder printing. Under the conditions of this Example, 10 point type was discernible but 16 and 20 point types were more clear. Of course, the ability to resolve the type is dependent on the porosity of the fabric substrate. Greater resolution is to be expected with fabrics of higher density.

A portion of the roll was coated with the resin used in Example 2 as described in that Example and sealed in pouches and tested as in said Example 2. The cured resin coated product showed the design more clearly and boldly than the printed uncured fabric. The accelerated aging test (at 150° F. (65.6° C.) in sealed aluminum foil pouches) showed no bleeding of the ink or premature curing of the casting tape roll, due to the ink.

Example 4. Flexoqraphic Printing with Crosslinkable Ink

The experiment of Example 2 was repeated using aqueous based Solvent Safe Ink SSK4009 in combination with 3 percent by weight Solvent Safe Crosslinker X1680 (available from Louis O. Werneke Co.). The test plate used was that used in Example 3. The finished product was again of high quality and the accelerated aging studies again showed no bleeding of the ink or premature curing due to the ink.

Example 5. Flexoqraphic Printing on Various Fabrics

Figure 2:
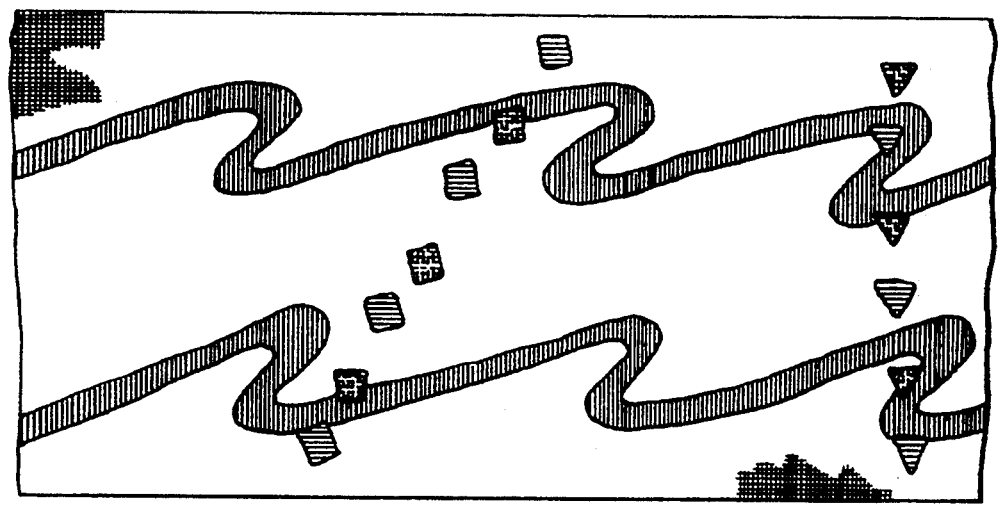
FIG. 2 is a representation of the pattern referred to in Example 5, lined for color.

Three 225 yd (206 m) rolls of four inch (10.2 cm) wide heat-set knitted fiberglass fabric (obtained as described in U.S. Pat. No. 4,609,578 ) were treated in various ways. Roll A was not treated further after knitting, Roll B was heat set and desized in an oven at 800° F. for 8 hours, and Roll C was steamed by direct heating with saturated steam (12-15 psig or 844-1055 g/cm²), then dried to set the starch sizing present on the fiberglass (about 1 to 1.5% by weight) as supplied by the manufacturer (PPG Industries, Lexington, N.C.). Each of these rolls was printed on a Webtron 51C. printing press (Webtron, F. Lauderdale, Fla.) at a line speed of 150 feet per minute (45.7 meters per minute) using each of three inks (3 color pattern). The drying zone temperature was about 38° C. after the ink was applied at ambient temperature (about 25° C.). In order to examine the print quality with respect to print image, stability and registration, a printing plate was used which has a party stripe pattern requiring registration. The pattern is shown in FIG. 2 of the drawings. The printing quality was good on each of the fabrics using the following inks available from Louis 0. Werneke Co.: Solvent Safe Yellow (SSYI), Blue 285 and Solvent Safe Red (SSR-4004). It was found that the registration was held much better with fabric rolls B and C. The printed fabrics were coated, converted and packaged using the procedure of Example 2. After aging in the 150° F. (66° C.) oven for several weeks it was found that the yellow printing bled slightly. The other printing was quite stable and showed no bleeding.

Example 6. Ink Jet Printing using a Matthews Marking System Division (available from Matthews International Corp., Pittsburgh, Pa.) non-continuous dot matrix printer with heads driven by a Compact Coder 2002 programmer, a 225 yard (206 m) roll of three inch (7.6 cm) wide heat-set desized fiberglass knit fabric was printed using three different inks as it was unwound before coating on the resin coater. Two print heads were used, one providing large characters with 16 jets per 2.5 inch (16 jets per 6.4 cm) and the other providing smaller characters with 16 jets per 1.25 inch (16 jets per 3.2 cm). The head using small characters provided clearer definition of the patterns. The inks used were Matthews inks Jam-4013 fast dry black, blue fast dry and green fast dry ink for nonporous substrates. The printed fabrics were coated, converted and packaged as in Example 2. The blue and black inks worked well, but the green ink bled significantly.

Example 7. Continuous Ink Jet Printing using a commercially available Matthews continuous ink jet printer (Model No. 4100) a 225 yd (206 m) roll of four inch (10.2 cm) wide heat-set knitted fiberglass fabric (comprised of ECG yarn (1.0, 0.72) knitted according to the Example of U.S. Pat. No. 4,609,578) was printed on line prior to coating with resin. The ink used was Matthews 219 black methyl ethyl ketone based ink. The printing head was positioned about one inch (2.54 cm) from the fiberglass knit which was running at 50 to 100 feet per minute (15 to 30 meters per minute). The unit printed an alphanumeric test pattern (A-Z, 0-9). The printed fabric was coated with the resin of Example 10 according to the method of Example 2. The coated fabric was converted into 12 foot (3.7 meter) rolls which were sealed in aluminum foil laminate pouches. The pouches were aged in an oven at 150° F. (65.6° C.). After several weeks of aging only slight bleeding of the ink was observed.

Example 8. Silk Screen Inks

A sample of three inch wide heat-set desized knitted fiberglass fabric of the same knit construction of Example 7 was printed by hand using both a round dowel pin and an ink stamp with the words "3M Restricted". The inks used were Radiant Orange SD-OG2434 and Magenta SD-MG2484 (available from Radiant Color Co., Richmond, Calif.) which adhered well to the fiberglass fabric to provide an attractive appearance.

Example 9. Full Coverage Flexographic Printing

Using the flexographic printing apparatus and the fiberglass fabric (both described in Example 5) a full coverage background printing with overprinting was carried out. The inks used were available from L.O. Werneke Co: Pink 210, Solvent Safe Yellow (SSYI), Warm Red (SSRP2) and Blue 285. Pink 210 was used as the full coverage background color and the yellow, red and blue were overprinted using a design of different space ship configurations. The printed fabric roll was then coated with the resin used in the previous Examples, the roll was converted into 4 yard (3.7 m) sections which were sealed in aluminum foil laminate pouches and the pouches were aged at 150° F. (65.5° C.) for several weeks. The colors were stable except for the yellow, which was observed to bleed slightly.

Example 10

Using the flexographic printing apparatus of Example 5 and a 225 yard (205.7 m) roll of four inch (10.2 cm) wide heat-set desized knitted fiberglass fabric made using ECG 75 1/0 0.7 fiberglass yarn (PPG Industries, Lexington, N.C.) according to the method of U.S. Pat. 4,609,578, the fabric was printed with a space ship design without a background color using 3 different inks at an ink temperature of about 38° C. and a line speed of 150 feet per minute (45.7 m/min). The inks, available from L.O. Werneke Co., were Solvent Safe Red 10004, Solvent Safe Blue 10007 and Solvent Safe Purple 10005. They were dried at 100° F. (43° C.). The printed fabric roll was then coated with resin described in Table 2 below at 39.5% by weight.

TABLE 2

| Ingredient | Equivalent Weight | Weight (%) | Weight (g) |
| --- | --- | --- | --- |
| Isonate 2143L (Dow Chemical Co.) | 1752.52 | 144.60 | 54.77 |
| para-Toluenesulfonyl Chloride | 1.6 | 190.00 | 0.05 |
| DB 100 silicone fluid (now known as Dow Corning Antifoam 1400) | N/A | 0.18 | 5.76 |
| Ionol ® (2,6-ditertiary) butyl 4-methyl phenol) | 248.00 | 0.48 | 15.36 |
| Pluronic F-108 (BASF Wyandotte) | 7250.00 | 4.00 | 128.0 |
| MEMPE Catalyst | 129.5 | 1.15 | 36.8 |
| Niax Polyol PPG-2025* | 1016.70 | 25.00 | 799.95 |
| NIAX Polyol LG-650* | 85.50 | 5.88 | 188.01 |
| NIAX E-562* polyol containing polymeric particles | 1781.00 | 8.50 | 272 |
| NCO/OH RATIO: | 3.84 | | |
| NCO EQUIV. WT.: | 357.00 | | |
| OH EQUIV. AVG.: | 439.76 | | |

*All available from A.C. West Virginia Polyols Corp., Wheeling, WV

The roll was converted into 30 4 yard (3.7 m) rolls which were sealed in aluminum foil laminate pouches as were control rolls of coated unprinted fabric. The pouches were aged at 150° F. (65.5° C.) for 3.5 weeks. The stability to aging was evaluated by measuring the force required to unwind each roll as a function of time using the test described herein below. The printed rolls showed excellent aging comparable to the control roll(s). No ink bleeding was observed in any of the printed rolls.

The casting articles were subjected to accelerate aging at a temperature of 65.5° C. (150° F.) as mentioned herein above. After cooling to 23-25° C. and equilibrating for 24 hours, the rolls were removed from the pouches and immediately unwound in such a manner that the force needed to unwind the rolls could be measured. Measuring of a force needed to unwind the roll was conducted using an Instron™ model 1122 tensile testing machine with a 50 lb (22.7 kg) load cell. Each roll was unwound counterclockwise from a freely rotating spindle over freely rotating cross-head spindle attached to the load cell of the tensile testing machine onto a 3.75 inch (9.84 cm) diameter takeup roller rotating a 60 revolution per minute, covered with stockinet (3M Ms04). The cross-head spindle consisted of a freely rotating 3/8 inch diameter by 5.5 inch long (0.95 cm × 14 cm) rod counter balanced to ensure that it hung in a horizontal position parallel to both the unwind spindle and the takeup roller. The force was measured by a Microcon™ model Mc4100 microprocessor, using the following machine conditions:

area=0
gauge length=4.5 inches (11.4 cm)
cross-head speed=0.1 inches per minute (0.254 cm/min)
stark force averaging at 0.0005 inches (0.00127 cm) (preset 0.8, elongation, 0.005)
endforce averaging at 0.0136 inches (0.0345 cm) (preset 0.9, elongation, 0.0136)
fail criteria=100%
load limit=43,360 kg force
cross-head stop=off
elongation correction factor=no correction The average force over 95.7 inches (24.3 cm) of tape was recorded as the unwind force (ignoring the first 3.65 inches (9.3 cm) tape).

The unwind force is measured for 5 rolls and the average values were obtained. The results indicated that upon accelerated aging the casting articles, prepared according to the invention and as described in the examples, exhibit unwind tension comparable to, and often superior to (i.e. less than) control materials.

Example 11

Figure 3:
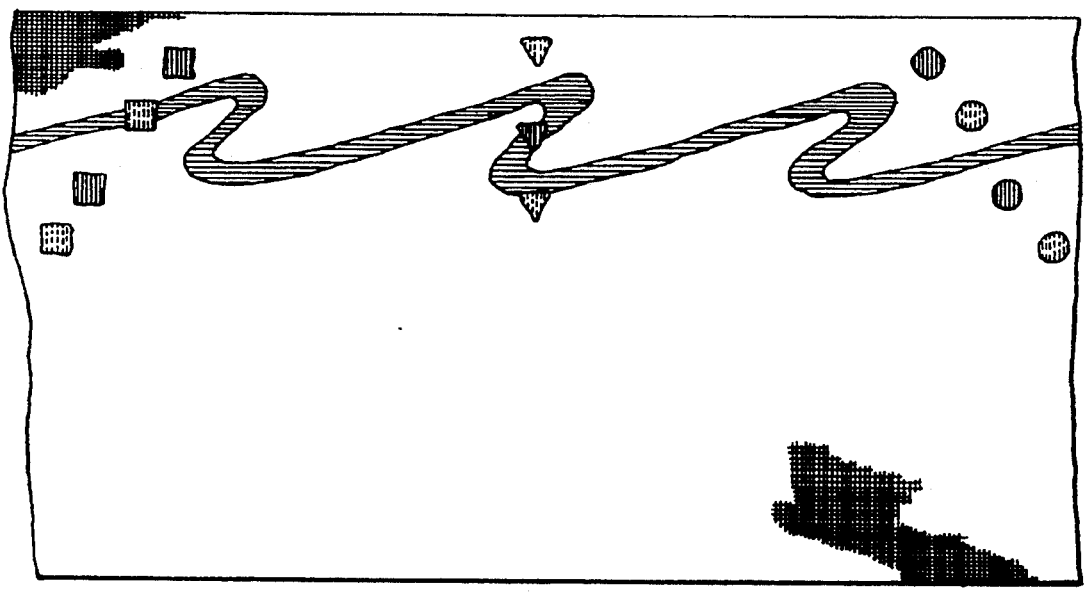
FIG. 3 is a schematic representation of the pattern referred to in Example 11.
Figure 4:
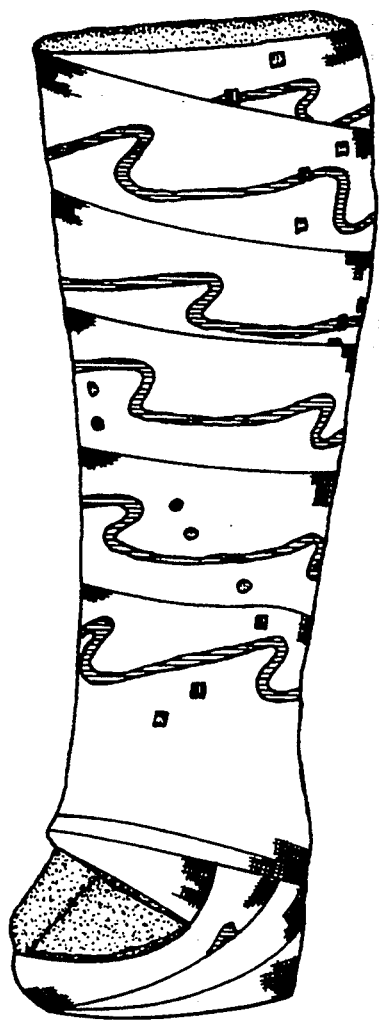
FIG. 4 is a schematic representation of the pattern illustrated in FIG. 3, shown wrapped in position for cure and illustrating lack of overlap of selected portions of printed pattern.

Using the flexographic printing appearance of Example 5, the inks of Example 10 and a roll of four inch (10.2 cm) wide heat-set desized knitted fiberglass fabric the printing plate was cut in half lengthwise and used to print only 50% of the fabric roll lengthwise i.e. only 50% of the width was printed. The printed fabric was then coated full width with the resin used in Example 5 to provide rolls of casting tape. When a roll of the casting tape was cured, by the usual technique of immersion in water, and applied to each arm, overlapping the non-printed side with each turn, an excellent pattern was obtained, due in part to the absence of a visible print pattern on the layer directly underneath. This is illustrated in FIGS. 3 and 4.

What is claimed is:

1. A casting tape comprising:
   a fiberglass substrate;
   an ink printed on said fiberglass substratein a preselected pattern, said ink comprising pigment particles in a binder, said binder serving to bind said pigment particles to an outer surface of said fiberglass substrate such that said pigment particles do not migrate; and
   a curable resin coated on said fiberglass substrate and over said preselected pattern of ink, said pigment particles and binder being relatively insoluble in said curable resin.

2. A casting tape according to claim 1 wherein:
said fiberglass substrate is at least 15% extensible in the machine direction; and
said curable resin is water curable.

3. A casting tape according to claim 2 wherein said curable resin comprises an isocyanate-functional polyurethane prepolymer.

4. A casting tape according to claim 1 wherein said preselected pattern of ink printed on said fiberglass substrate comprises a multicolored pattern.

5. A casting tape according to claim 1 wherein the pigment in said pigment particles is selected from the group consisting of phthalocyanine pigments, dioxazine pigments, diazo pigments, anthraquinone pigments, quinacridone pigments, perylene pigments, isoindolinone pigments, and mixtures thereof.

6. A casting tape according to claim 1 wherein the pigment in said pigment particles is selected from the group consisting of the following Colour (Index Pigments: Blue 15.3; Red 202; Green 7; Red 166; Red 178; Yellow 109; Violet 23; Red 242; Red 122; Red 254; Black 7; White 6; Violet 19; Violet 42; and mixtures thereof.

7. A casting tape according to claim 6 wherein said pigment particles comprises pigment in a chip form.

8. A casting tape according to claim 1 wherein said ink printed on said fiberglass substrate is provided substantially free of tertiary amines such that the shelf stability of said resin is not significantly adversely affected.

9. A casting tape according to claim 1 wherein said binder is selected from the group consisting of: acrylic and polyurethane resins; polymers made from ethylene vinyl acetate, polyvinyl alcohol, polyvinylpyrrolidone, and mixtures thereof; ethylene propylene copolymers; polyisobutylene; polyisoprene; butyl rubber; natural rubber; synthetic rubber; polyesters; and mixtures thereof.

10. A method of preparing an orthopedic casting tape, said method comprising the steps of:
providing a fiberglass substrate;
mixing pigment particles with a binder;
printing the pigment particles and binder as a pattern on the fiberglass substrate to form a printed fiberglass substrate, the binder serving to bind the pigment particles to an outer surface of the fiberglass substrate such that the pigment particles do not migrate; and
applying a curable resin to the printed fiberglass substrate, the pigment particles and binder being relatively insoluble in the curable resin.

11. A method according to claim 4 wherein said step of printing comprises printing a multicolored pattern.

12. A method according to claim 11 wherein said step of printing comprises a step of flexographic printing.

13. A method according to claim 11 wherein said step of printing comprises a step of flexographic printing.

14. A method according to claim 10 wherein the pigment in said pigment particles is selected from the group consisting of the following Colour Index Pigments: Blue 15.3; Red 202; Green 7; Red 166; Red 178; Yellow 109; Violet 23; Red 242; Red 122; Red 254; Black 7; White 6; Violet 19; Violet 42; and mixtures thereof.

15. An orthopedic casting tape made according to the method of claim 14.

16. An orthopedic casting tape made according to the method of claim 10.

17. A cured article comprising:
a fiberglass substrate having ink printed thereon in a preselected pattern, said ink comprising pigment particles in a binder, said binder serving to bind said pigment particles to an outer surface of said fiberglass substrate such that said pigment particles do not migrate; and
a cured resin coated on the fiberglass substrate and over said preselected pattern of ink, the pigment particles and binders being relatively insoluble in the resin prior to being cured.

18. A casting tape according to claim 3 wherein the pigment in said pigment particles is selected from the group consisting of phthalocyanine pigments, dioxazine pigments, quinacridone pigments, perylene pigments, isoindolinone pigments, and mixtures thereof.

19. A casting tape according to claim 3 wherein said binder is selected from the group consisting of acrylic resins, polyurethane resins, and mixtures thereof.

20. A method according to claim 10 wherein the pigment in said pigment particles is selected from the group consisting of phthalocyanine pigments, dioxazine pigments, quinacridone pigments, perylene pigments, isoindolinone pigments, and mixtures thereof.

21. A method according to claim 10 further comprising the step of desizing the fiberglass substrate before said printing step.

22. A method according to claim 10 further comprising the step of heat setting the fiberglass substrate before said printing step.

23. A method according to claim 10 further comprising the step of starch setting the fiberglass substrate before said printing step.

24. A casting tape according to claim 1 wherein said binder comprises a polymer made from ethylenically unsaturated monomers.

25. A casting tape according to claim 1 wherein said ink is a gelation ink.

26. A casting tape according to claim 1 wherein said ink is a gelation ink comprising fine particles of PVC resin in a plasticizer.

27. A casting tape according to claim 1 wherein said ink is an aqueous based ink.

28. A casting tape according to claim 1 wherein said ink is an organic solvent based ink.

29. A method according to claim 10 wherein said binder comprises a polymer made from ethylenically unsaturated monomers.

30. A method according to claim 10 wherein said particles and binder are in the form of a gelation ink.

31. A method according to claim 10 wherein said particles and binder are in the form of a gelation ink comprising fine particles of PVC resin in a plasticizer.

32. A method according to claim 10 wherein said particles and binder are in the form of an aqueous based ink.

33. A method according to claim 10 wherein said particles and binder are in the form of an organic solvent based ink.

34. A method according to claim 10 wherein said step of printing comprises a step of silk screen printing.

35. A method according to claim 10 wherein said step of printing comprises a step of hot melt screen printing.

* * * * *

UNITED STATES PATENT AND TRADEMARK OFFICE
CERTIFICATE OF CORRECTION

PATENT NO. : 5,342,291
DATED : August 30, 1994
INVENTOR(S) : Matthew T. Scholz et al.

It is certified that error appears in the above-indentified patent and that said Letters Patent is hereby corrected as shown below:

Col. 13, line 39, " 4' " should be --4"--.

Col. 13, line 43, " 4' " should be --4"--.

Col. 18, line 59, in claim 1, line 3, "substratein" should be --substrate in--.

Col. 19, line 19, claim 6, line 3, delete "(" before "Index".

Col. 19, line 25, claim 7, line 2, "comprises" should be --comprise--.

Col. 19, line 52, claim 11, line 1, "4" should be --10--.

Col. 19, line 56, claim 13, line 1, "11" should be --10--.

Col. 20, line 12, claim 17, line 10, "binders" should be --binder--.

Signed and Sealed this

Third Day of January, 1995

Attest:

BRUCE LEHMAN

Attesting Officer

Commissioner of Patents and Trademarks

Adverse Decision in Interference

Patent No. 5,342,291, Matthew T. Scholz, Michael D. Delmore, Daniel W. Davis, PRINTED WOVEN FIBER MATERIALS AND METHOD, Interference No. 105,458, final judgment adverse to the patentees rendered April 5, 2007, as to claims 1-35.

(*Official Gazette* June 12, 2007)